United States Patent [19]

Talley, III

[11] Patent Number: 4,982,609

[45] Date of Patent: Jan. 8, 1991

[54] TEST DEVICE FOR VEHICLE ROOF STIFFNESS

[75] Inventor: Walter D. Talley, III, Mount Clemens, Mich.

[73] Assignee: Chrysler Corporation, Highland Park, Mich.

[21] Appl. No.: 500,448

[22] Filed: Mar. 26, 1990

[51] Int. Cl.⁵ .................................. G01N 3/20
[52] U.S. Cl. ........................................ 73/849
[58] Field of Search .................. 73/788–792, 73/849, 852, 853, 865.3, 865.4, 865.8, 865.9

[56] References Cited

U.S. PATENT DOCUMENTS

| | | | |
|---|---|---|---|
| 4,101,061 | 7/1978 | Sage et al. | 248/231.4 |
| 4,108,719 | 8/1978 | Olshausen | 73/789 |
| 4,213,349 | 7/1980 | Miura | 73/852 |
| 4,589,288 | 5/1986 | Porter et al. | 73/852 |
| 4,830,908 | 5/1989 | Nakajima et al. | 428/246 |

FOREIGN PATENT DOCUMENTS 578424 11/1931 Fed. Rep. of Germany ........ 73/789

Primary Examiner—Robert Raevis
Attorney, Agent, or Firm—Edward P. Barthel

[57] ABSTRACT

An apparatus for use in measuring the roof panel stiffness of an automatic vehicle having a unitized steel body construction. The apparatus comprises a support structure for positioning an upper cross beam assembly in a spaced exterior manner above the roof panel. The cross beam assembly comprising an upper arch beam and a lower lever arm having one end pivotally connected to one side of the cross beam for supporting a load cell on the roof panel upper surface. A low voltage displacement transducer is supported between the arch beam and the lever arm in vertical alignment with the load cell. Loads applied to the free end of the lever arm are measured by the load cell while resultant deflections are measured by the transducer. The transducer and load cell are adapted to be electrically connected to an X-Y plotter, so as to provide a load/deflection curve for the roof panel.

7 Claims, 5 Drawing Sheets

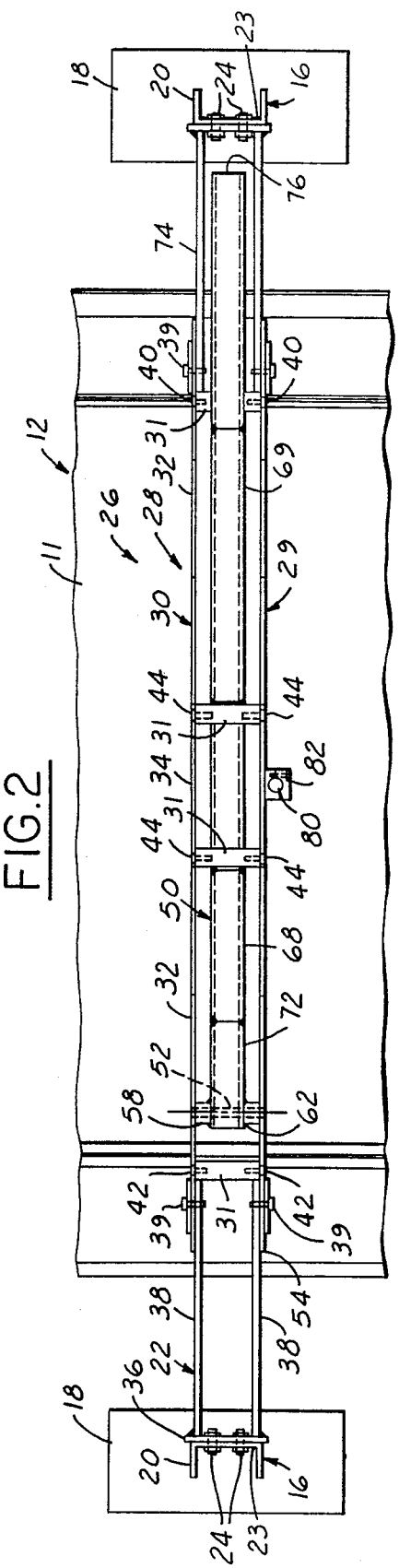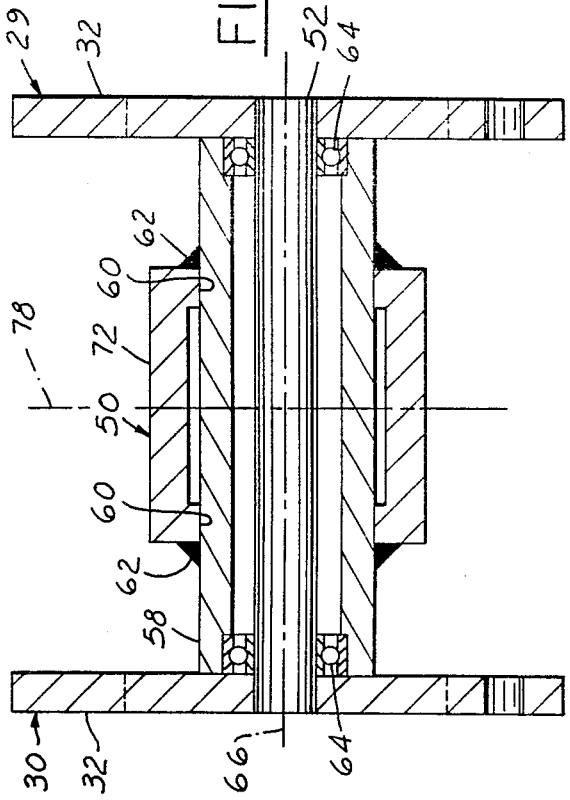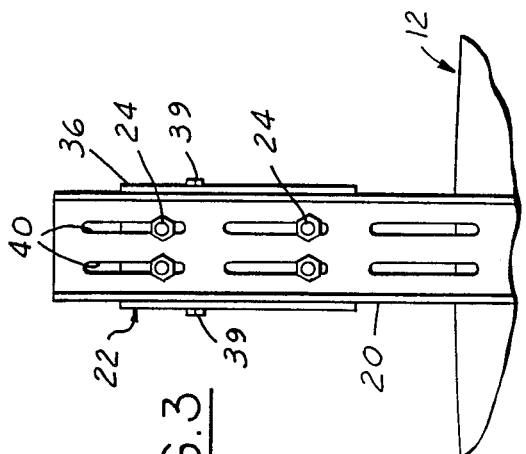

TEST DEVICE FOR VEHICLE ROOF STIFFNESS

BACKGROUND OF THE INVENTION

This invention relates to a test device for automotive vehicles and more particularly to an apparatus for measuring the stiffness of a vehicle body roof panel structure.

SUMMARY OF THE INVENTION

It is an object of the present invention to provide a load fixture test apparatus for accurately applying and measuring the load/deflection stiffness of a vehicle body roof panel structure.

It is another object of the present invention to provide a load fixture test apparatus as set forth above wherein the apparatus, in a first stationary form, includes a cross-beam measuring assembly for accurately measuring the stiffness of the vehicle body roof panel structure wherein the cross beam assembly is supported independently of the roof panel by a frame which straddles a vehicle enabling one or more vehicle roof panels to be readily tested in a "drive through" manner at a test facility.

It is still another object of the present invention to provide a test apparatus as set forth above wherein the apparatus, in a second transportable form, includes a cross-beam measuring assembly for accurately measuring the stiffness of vehicle body roof panel structures wherein the cross beam assembly is supported independently of the roof panel by a pair of dual clamping assemblies positioned in opposed side door window openings adapted for ready adjustable attachment to and removal from vehicle bodies of varying sizes such as subcompact, compact, basic middle, basic large etc.

In accordance with the invention the apparatus comprises a common cross beam assembly that may be supported in a spaced independent manner of a vehicle roof panel exterior surface by either of two alternative mounting arrangements. The first mounting arrangement is in the form of a stationary frame which is adapted to straddle a vehicle drive-in or drive-through stall enabling one or more vehicle roof panels to be readily tested at an established site.

The second mounting arrangement enables the common cross beam assembly to be transported to a particular vehicle to be tested and readily attached to the vehicle independent of the roof panel by means of a pair of mirror image dual left side and right side clamping assemblies. The dual clamping assemblies are adapted to be partially inserted through opposed side door window frame openings of the vehicle. Consequently, the dual clamping assemblies are uniquely designed for ready fore and aft spacing relative to the transversely extending cross beam assembly to accommodate for differences in size of the vehicle window frame openings. Further, each of the clamping assemblies are adapted for lateral adjustment on the cross beam assembly enabling the test apparatus to be adjustably mounted in a ready manner on vehicles of varying transverse dimensions.

The common cross beam assembly includes an upper arch beam and a lower lever arm having one end pivotally connected to one side of the beam for swinging movement in the beams vertically disposed transverse plane of symmetry. The lever arm supports a load cell on the vehicle roof panel outer surface operative to sense a force applied to the vehicle roof panel that is directly proportional to an incremental load applied by the lever arm. A low voltage differential displacement transducer is supported between the upper arch beam and the lower lever arm. A read-out X-Y plotter, electrically connected to both the transducer and the load cell is readable to identify and record the extent of load/deflection undergone by the vehicle roof panel when incremental amplified loads are applied to the lever arm providing a measure of the flexure rigidity of the panel.

BRIEF DESCRIPTION OF THE DRAWINGS

These and other objects, features and advantages of the invention will appear from the following written description and the accompanying drawings in which:

FIG. 2 is a fragmentary top elevational view taken on the line 2—2 of FIG. 1;

FIG. 3 is a fragmentary side elevational view taken on the line 3—3 of FIG. 1;

FIG. 4 is an enlarged sectional view taken on the line 4—4 of FIG. 1;

DETAILED DESCRIPTION OF THE INVENTION

Figure 1:
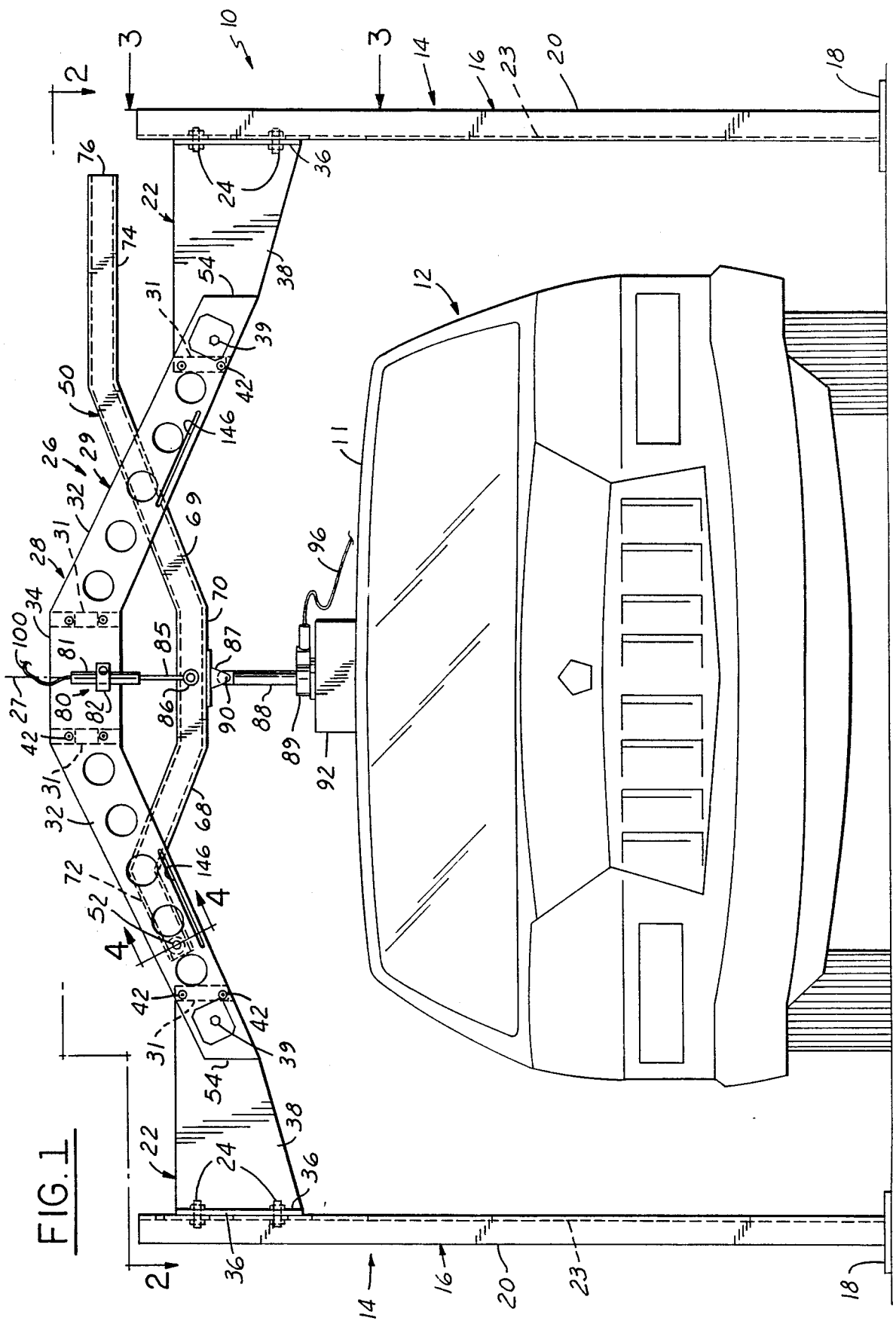
FIG. 1 is a front elevational view showing a first embodiment of the invention.

Referring now to the drawings and in particular to FIG. 1 the first embodiment of a load fixture test apparatus 10 for attaining an accurate application and measure of roof panel load/deflection. Loads are applied to a roof panel 11 of an automotive vehicle unitized steel body 12 in a test facility. The test apparatus 10 comprises a gantry type support frame, generally indicated at 14, including a pair of identical laterally spaced side supports 16 disposed on each side of the vehicle body 12. Each of the side supports 16 has a base 18 an upright channel post 20 and an inwardly projecting end mounts 22 with the end mounts 22 adapted to be adjustably secured to associated post webs 23 as by bolts 24 adjacent the inboard upper ends of their associated posts 20.

The side supports 16 are interconnected by a cross beam assembly generally indicated at 26. The cross beam assembly 26 is supported independent of the roof panel 11 and is symmetrical about a longitudinally extending vertical plane of symmetry which includes a dashed construction line 27. The cross beam assembly 26 comprises an arch beam 28 having forward 29 and aft 30 spaced parallel webs secured in spaced relation by four uniformly positioned rectangular shaped spacer blocks 31.

The arch beam 28 has a pair of outwardly and downwardly sloped or diverging flank sections 32 joined by a upper horizontal center section 34. As best seen in FIGS. 2 and 3 the pair of end mounts 22 each have a butt plate 36 welded to parallel gussets 38 with their inboard ends secured to an associated flank section 32 outboard end by the bolts 39 (FIG. 3). Each post web 23 has a plurality of elongated paired slots 40 (FIG. 3) to enable the end mounts 22 to be adjustably secured by bolts 24 for vertical movement relative to their respective posts 20. Bolts 42 are provided to secure the cross beam webs 29 and 30 to each of the spacer blocks 31.

The cross beam assembly 26 further comprises a box sectioned lever arm, generally indicated at 50 in FIG. 1. Lever arm 50 has one left hand end pivotally supported by pivot pin 52 intermediate arch bend one free outboard end 54 and its juncture with the center section 32. The box sectioned lever arm is sized for nested reception between the fore and aft webs 29 and 30 the arch beam 28. As seen in FIG. 4 the lever arm 50 has a transverse sleeve 58 extending through aligned holes 60 in the lever arm 50 with the sleeve 58 welded thereto at welds 62. Inner ball bearings 64 surround the pivot pin 52 so as to journally support the pivot pin 52 within the sleeve 58 enabling the lever arm 50 to swing about longitudinally extending pivot pin axis 66. It will be noted in FIG. 1 that the lever arm 50 has an inverted arch or trough shape comprising outwardly and upwardly diverging flank sections, in the form of a lower short flank section 68 and a lower long flank section 69, joined by a lower substantially horizontal center section 70.

With reference to FIGS. 1 and 2 the left hand flank section 68 of the lever arm 50 is connected to the pivot pin 52 by a downwardly and outwardly pivot mounting angled section 72. It will be noted in FIG. 1, with the lever arm 50 in its initial position or neutral zero setting, the pivot pin angled section 72 is substantially parallel to the left hand flank section 32 of the arch beam 28 while its lower central section 70 is parallel to the upper central section 34 of the arch beam 28. It will be seen in FIG. 1 that the long flank section 69 terminates at its outboard end in a horizontally extending loading limb section 74 which projects outboard over its associated mount 22 which terminates just short of the post 20.

With respect to FIG. 4 it will be seen that the transversely extending vertical disposed medial plane of symmetry of arch beam 28, which includes its vertical neutral axis 78, coincides with the transversely extending vertically disposed medial plane of symmetry of the lever arm 50.

Figure 11:
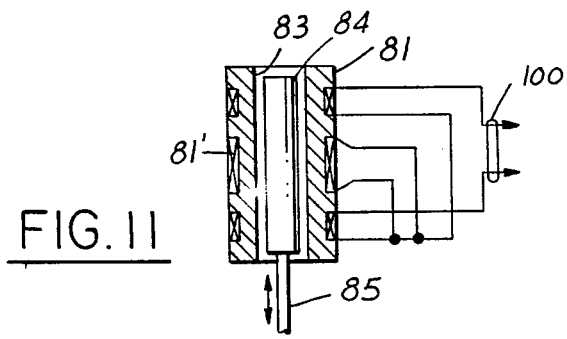
FIG. 11 is a fragmentary schematic cross sectional drawing of a linear displacement transducer used with the present invention.

FIG. 1 shows a linear measurement sensor in the form of a reluctive (LVDT) linear displacement transducer (linear variable differential-displacement transformer) generally indicated at 80. The linear displacement transducer 80 comprises an outer cylindrical case 81 supported by a clamp 82 on the upper center section 34 of the cross beam 30. As seen, for example, in the schematic view of FIG. 11 the case 81 includes coils 81' and has an axial bore liner 83 within which an armature or core 84 moves. The lower end of the core 84 is threaded to accept a sensing shaft 85 which is substantially aligned on the vertical plane of symmetry indicated by the construction line 27 in FIG. 1.

The lower end of the sensing shaft 85 is connected to a universal journal connection 86 fixed to forward face of the lever arm lower center section 70. In the disclosed embodiment the transducer 80 is manufactured and sold by Schaevits Engineering and is described in their technical bulletin 1002E. Reference may be made to pages 93–96 of the book titled "Sensor And Analyzer Handbook" by Harry N. Norton published in 1988 by Prentice Hall, Inc., for a discussion of the operation of a typical linear displacement transducer.

In FIG. 1 the lever arm lower center section 70 is shown having a pivot bracket 87 fixed to its undersurface supporting a depending rod 88 with a compression load cell 89 secured to its lower end for pivotal movement about the axis of a longitudinally extending rod pivot pin 90. The compression load cell 89 of the present invention is a "Flat Load Cell" manufactured and sold by The Strainsert Company, Union Hill Industrial Park, West Conshohocken, Pa. 19428.

The load cell 89 is shown resting on a spacer member, such as a wooden block 92, supported intermediate the load cell 89 and the upper surface of vehicle roof panel 11. Upon predetermined loads being slowly applied to the wooden block 92 by the loading limb section 74 of the lever arm 50 the compression load cell 89 measures the magnitude of the load in pounds applied to the vehicle roof panel 11 while the transducer 80 records the downward linear travel or deflection in inches of the roof panel 11. The rod pivot pin 90 operates to maintain the principal axis of the rod 88 aligned in the vertical plane of construction line 27.

Figure 12:
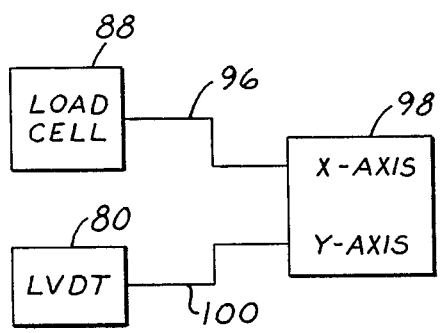
FIG. 12 is a typical circuit block diagram to accomplish measurement and plotting of a vehicle roof load/deflection curve according to the invention.

With reference to the schematic diagram of FIG. 12 it will be seen that the compression load cell 89 may be electrically connected by cable 96 to the "Y" axis of an X-Y plotter 98 to record loading in pounds. In a similar manner the LVDT deformation transducer 80 is electrically connected by cable 100 to the "X" axis of the X-Y plotter 98 recording deflections in inches. Thus, a load/deflection curve is recorded by the X-Y plotter 98 for the particular vehicle roof panel 11 being tested.

With reference to FIGS. 5–10 of the drawings there is shown a second embodiment of the invention adapted to be transportable to a remote site, for example, to accomplish a roof stiffness test for automotive vehicles without requiring the use of the side supports 16 and 20. The second transportable embodiment is designed for use in field testing situations wherein it is readily adjustable for mounting on various sized vehicles such as subcompact, compact, basic middle, basic large etc. This is to be contrasted with the first relatively stationary embodiment of FIGS. 1–4 which is designed to measure load/deflection of vehicle roof panels in a "drive through" manner at a test facility. It will be noted, however, that the load fixture cross beam assembly 26' has identical components as the assembly 26 described in FIGS. 1–4. Thus, the second embodiment of FIGS. 5–10 provides an alternate support means for mounting the cross beam assembly 26' to a vehicle for testing the roof panel 11 independent of the vehicle suspension system. Like or similar components disclosed in FIGS. 5–10 are given the same reference numerals applied to FIGS. 1–4 components except that they are primed.

Figure 5:
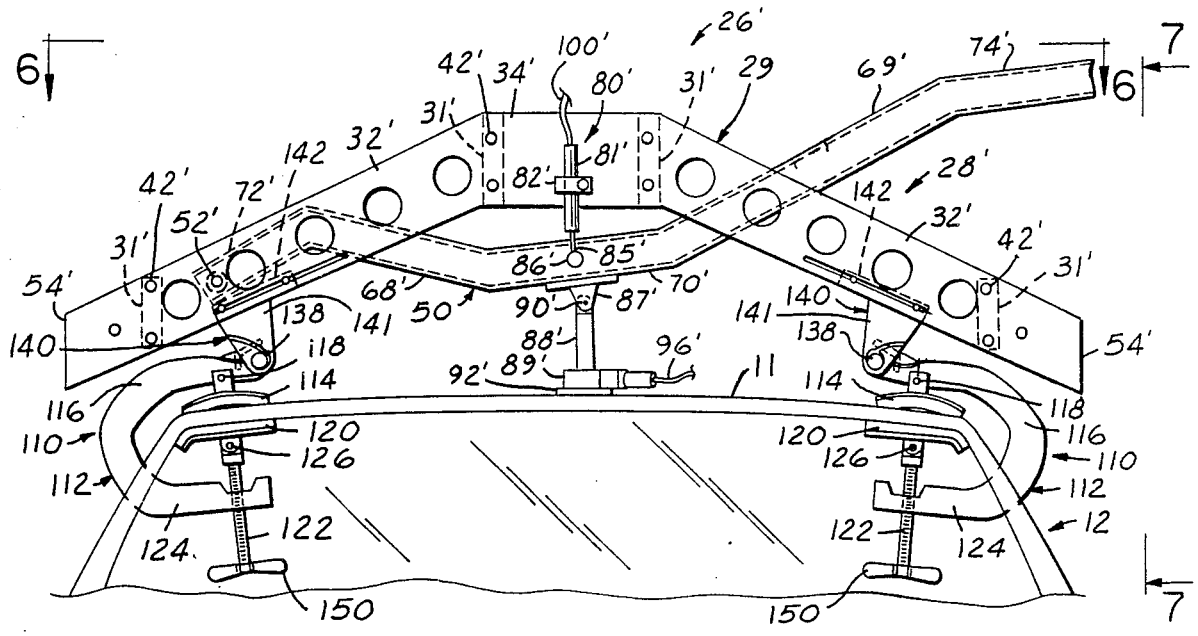
FIG. 5 is a fragmentary front elevational view showing a second embodiment of the invention.
Figure 6:
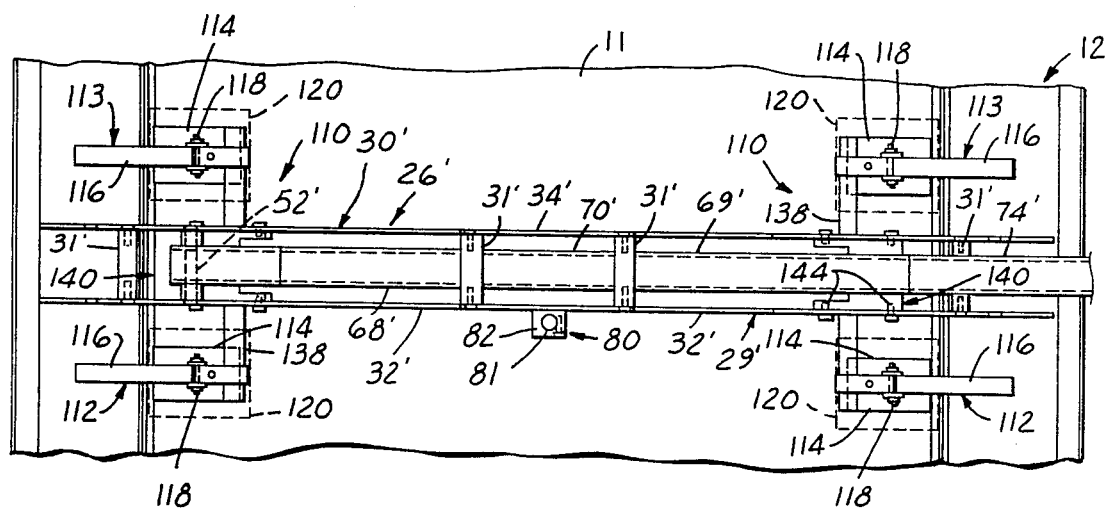
FIG. 6 is a fragmentary top elevational view taken on the line 6—6 of FIG. 5.
Figure 7:
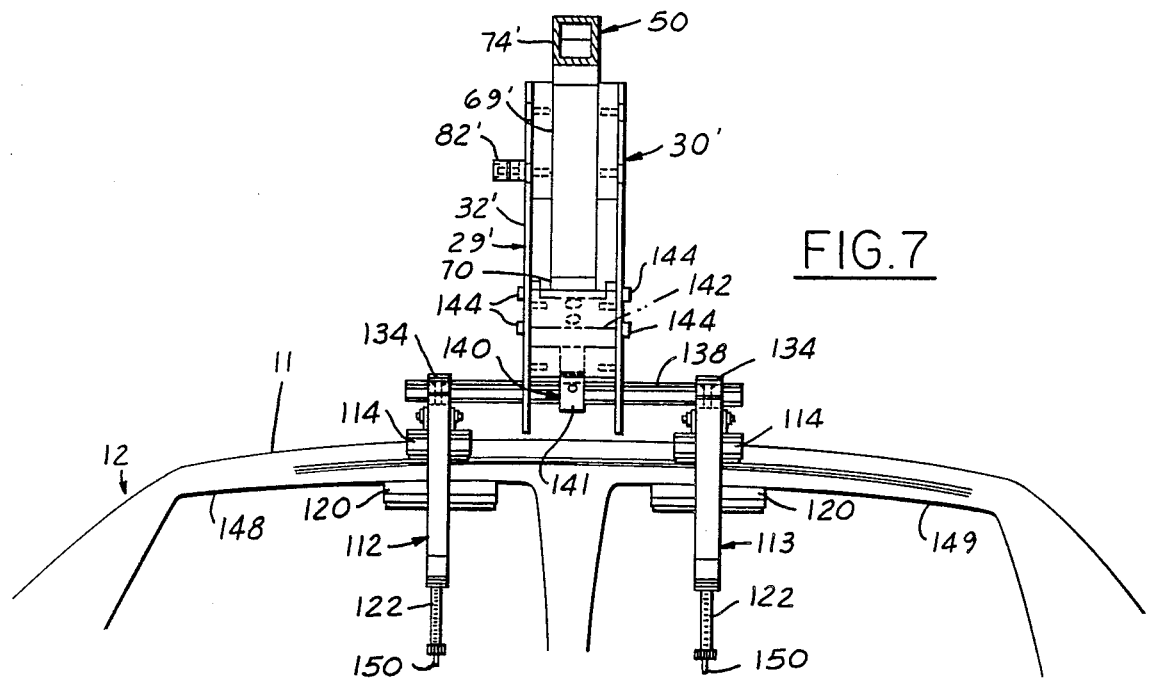
FIG. 7 is a fragmentary side elevational view taken on the line 7—7 of FIG. 5.
Figure 8:
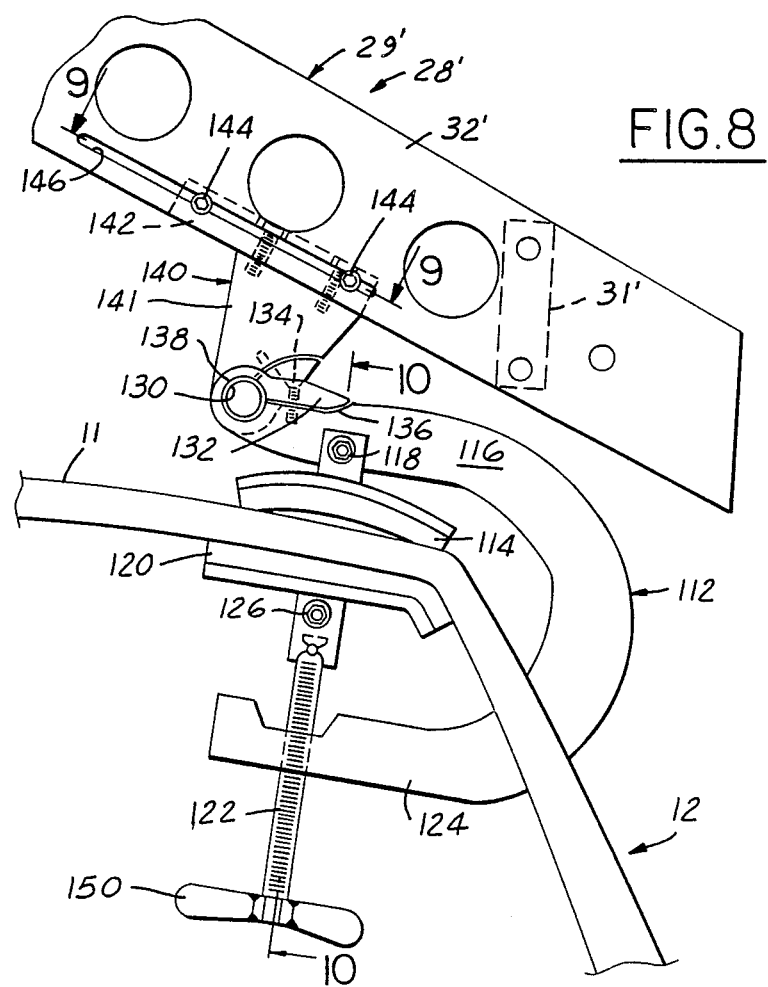
FIG. 8 is an enlarged fragmentary view of the right hand clamping arrangement of FIG. 5.
Figure 9:
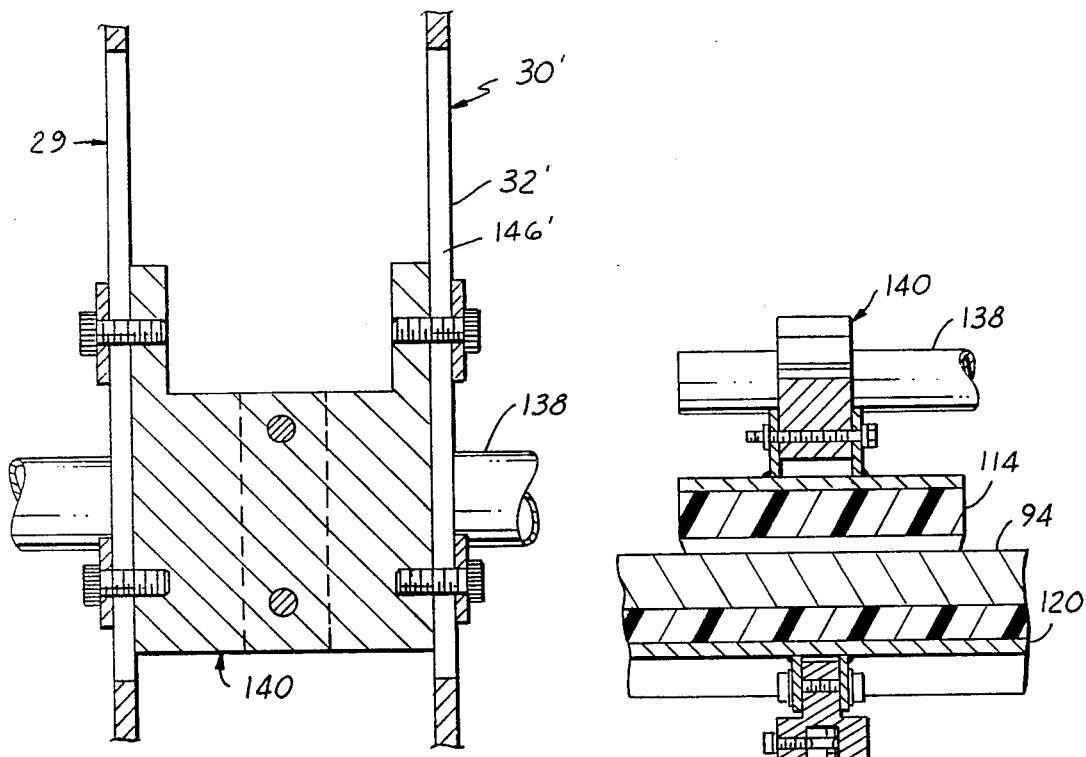
FIG. 9 is an enlarged fragmentary sectional view taken on the line 9—9 of FIG. 8.

As seen in FIGS. 5, 6, and 7 left and right identical clamp assemblies 110 are provided to support the load fixture cross beam assembly 26' in an independent manner spaced above the vehicle roof panel 11. Each clamp assembly 110 comprises a pair of fore 112 and aft 113 C-clamps with each C-clamp having an outer jaw 114 pivotally mounted to upper clamp leg 116 for movement about a longitudinal axis of an outer jaw pin 118. An inner jaw 120 is movably mounted to one end of an adjustment clamping screw 122 threadably engaging lower leg 124 with the inner jaw 120 pivotally mounted to the clamping screw 122 for movement about the longitudinal axis of an inner jaw pin 126. As best seen in FIGS. 7 and 8 each of the fore 112 and aft 113 C-clamps has its upper leg 116 free end formed with a split opening 130 defining a retaining tongue portion 132 having a screw 134 threaded in aligned bores bridging split 136 in each leg 116.

Figure 10:
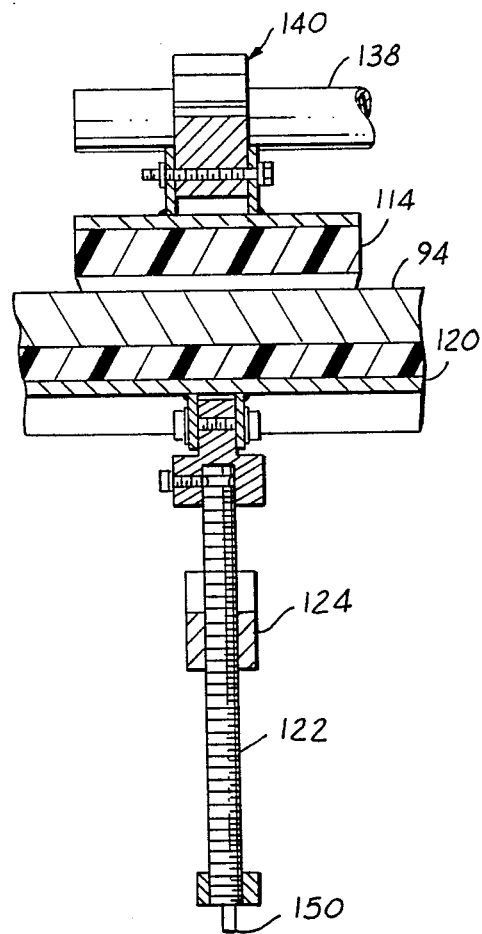
FIG. 10 is an enlarged fragmentary sectional view taken on the line 10—10 of FIG. 8.

A longitudinal tube 138 is shown in FIGS. 5 and 10 having an adjustable mount 140, including a depending ear 141, with the mount 140 adjustably positioned intermediate the beam fore 29 and aft 30 webs by a mounting block portion 142. Screws 144 extend through elongated positioning slots 146' in each of the beam webs 29' and 30' as seen in FIG. 8. The positioning slots 146' allow each left and right mount 140 to be adjustably moved inboard from its outermost position of FIG. 5 to accommodate narrower width vehicles having a smaller transverse dimension. It will be appreciated that the angled section 72 of the lever arm 50 functions to allow clearance of its associated adjustable mount 140.

Each adjustable mount depending ear 141 has a split circular opening 130 (FIG. 7) through which its associated tube 138 extends such that its fore and aft ends are longitudinally adjustably received in associated C-clamp aligned openings 130 to accommodate longitudinal variations in vehicle window sizes.

It will be seen in FIG. 7 that with vehicle front side 148 and rear side 149 windows lowered each forward C-clamp 112 and each aft C-clamp 113 lower leg 124 extends through an associated open window such that their inner jaws 120 contact the roof inner headliner while their outer jaws 114 contact the outer surface of the roof panel 11. Upon the clamping screws 122 being manually turned by their hand grips 150 the C-clamp inner and outer jaws are brought into tight engagement with their respective roof and headliner surfaces such that the cross beam assembly 26' is securely fixed on the vehicle enabling the roof to be tested in the same manner as described for the first embodiment of FIGS. 1–4.

While the principles of the present invention in connection with the specific test device has been described, it is to be understood the foregoing detailed description has been made by way of example only and not as a limitation to the scope of the invention as set for in the accompanying claims.

What is claimed is:

1. A testing apparatus for measuring roof panel stiffness of an automobile vehicle steel body, the apparatus comprising:

a cross beam measuring assembly comprising a symmetrical arch beam member and a force applying trough-shaped lever arm, said arch beam member adapted to be positioned by a pair of laterally spaced support means in a transverse vertically spaced manner above the roof panel of said vehicle body, said cross beam assembly arch beam member having first and second outwardly and downwardly diverging mirror image flank sections interconnected by a horizontal arch beam member center section, whereby said center section has its midpoint coinciding with the longitudinal plane of symmetry of said vehicle body;

said trough-shaped lever arm formed with outwardly and upwardly diverging first short and second long flank sections interconnected by a lever arm center section, means pivotally mounting said lever arm first short flank section on said arched beam member first flank section for pivoting in a transversely extending vertically disposed plane including the transversely extending vertically disposed medial plane of symmetry of said arch beam member;

said lever arm second long flank section having its outboard end connected to a loading limb projecting outboard in substantially parallel relation to said lever arm center section so as to overlie an associated one of said pair of support means, whereby said lever arm center section is disposed in substantially parallel vertically spaced subjacent relation to said arch beam member center section with said cross-beam measuring assembly in its zero setting;

linear displacement transducer measuring means interconnected between said arch beam member center section and said lever arm center section for measuring the downward movement of said lever arm center section relative to said arch beam member center section related to downward forces applied to said lever arm loading limb;

rod means pivotally mounted in a vertically disposed manner on said lever arm center section, said rod means having compression load cell measuring means fixed on its lower end, spacer means positioned intermediate said load cell measuring means and a central exterior surface portion of said vehicle body roof panel with said cross-beam assembly lever arm in its zero setting; and whereby upon the application of a predetermined downward incremental force to said lever arm loading limb said load cell measuring means senses a resultant amplified force applied via said spacer means to said vehicle body roof panel central portion, said resultant amplified force being directly proportional to said predetermined downward incremental force applied to said lever arm causing a corresponding downward deflection of said vehicle body roof panel central portion.

2. The testing apparatus as set forth in claim 1, wherein read out means are electrically connected to both said transducer measuring means and said load cell measuring means, said read out means readable to identify the extent of deflection undergone by said vehicle body roof panel central portion when said predetermined downward incremental force is applied to said lever arm providing a measure of the flexure rigidity of said vehicle body roof panel central portion.

3. The test apparatus as set forth in claim 1, wherein said pair of laterally spaced support means comprises upright posts disposed on each side of said vehicle body each having upper and lower ends, mounting means secured adjacent the upper end of each said post, each said first and second flank section connected adjacent its outboard end to an associated post mounting means such that said arch beam member defines with said pair of posts a symmetrical support frame adapted to straddle said vehicle body.

4. The testing apparatus as set forth in claim 3, wherein each said mounting means is adjustably fixed to its associated post enabling vertical adjustment thereof.

5. The testing apparatus as set forth in claim 1, wherein said support means comprises a pair of clamping assemblies, each said clamping assembly including an adjustable mount attached to an associated arch beam member flank section adjacent its outboard free end, each said clamping assembly adapted to be inserted in an opposed side door open window frame of said vehicle body for releasably clampingly engaging an associated outboard portion of the vehicle roof panel.

6. The testing apparatus as set forth in claim 5, wherein each said clamping assembly adjustable mount adapted to be selectively moved inboard from an outermost position on its associated arch beam flank section to accommodate narrower width vehicles.

7. The testing apparatus as set forth in claim 6, wherein each said clamping assembly comprises a pair of longitudinally spaced C-clamps supported on a longitudinally extending tube with each said tube fixed to its associated adjustable mount, and each said C-clamp is adapted for fore and aft adjustment on its associated tube.

* * * * *